United States Patent [19]

Hawkins

[11] Patent Number: 4,473,456
[45] Date of Patent: Sep. 25, 1984

[54] CONDUCTIMETRIC GAS SENSOR

[75] Inventor: Peter Hawkins, Frenchay, England

[73] Assignee: National Research Development Corporation, London, England

[21] Appl. No.: 360,769

[22] Filed: Mar. 22, 1982

[30] Foreign Application Priority Data

Apr. 8, 1981 [GB] United Kingdom ................ 8111043

[51] Int. Cl.³ .......................................... G01N 27/26
[52] U.S. Cl. .................... 204/414; 204/1 T; 204/415; 204/403; 324/439; 324/459
[58] Field of Search ........... 204/195 P, 195 M, 195 R, 204/1 T, 1 K, 415; 324/439, 459

[56] References Cited

U.S. PATENT DOCUMENTS

| | | | |
|---|---|---|---|
| 3,483,112 | 12/1969 | Ross | 204/1 T |
| 3,856,649 | 12/1974 | Genshaw et al. | 204/195 M |
| 3,886,058 | 5/1975 | Barna | 204/195 P |
| 3,957,613 | 5/1976 | Macur | 204/414 |
| 3,961,895 | 6/1976 | Frenyo | 324/439 |
| 4,049,503 | 9/1977 | Becker et al. | 204/414 |
| 4,227,974 | 10/1980 | Petersen et al. | 204/414 |
| 4,269,685 | 5/1981 | Parker | 204/414 |
| 4,324,256 | 4/1982 | Vesterager | 204/403 |
| 4,326,200 | 4/1982 | Bushman | 204/195 R |
| 4,352,884 | 10/1982 | Nakashima et al. | 204/403 |

FOREIGN PATENT DOCUMENTS

| | | | |
|---|---|---|---|
| 1442303 | 7/1976 | United Kingdom | 204/403 |
| 1558251 | 12/1979 | United Kingdom | 204/403 |

OTHER PUBLICATIONS

Rechnitz, "Membrane Bioprobe Electroder", Jan. 27, 1975, C&EN, pp. 29–35.
Scarano & Calcagno, Analytical Chemistry, vol. 47, No. 7, pp. 1055–1065, Jun. 1975, High Sensitivity Carbon Dioxide Analyzer.
H. A. Himpler et al., Conductimetric Gas Sensor for Carbon Dioxide, Analytical Chemistry, vol. 50, No. 12, Oct. 1978, pp. 1623–1627.
Karl Lis Helmut Acker et al., Instruments and Techniques A. PCO₂ Surface Electrode Working on the Principle of Electrical Conductivity, 1979, pp. 289–291.
Dawood Parker et al., Single Electrochemcial Sensor for Transcutaneous Measurement of PO₂ and PCO₂, Birth Defects: Original Article Series, vol. XV, No. 4, pp. 109–116, 1979, The National Foundation.

Primary Examiner—T. Tung
Assistant Examiner—Terryence Chapman
Attorney, Agent, or Firm—Cushman, Darby & Cushman

[57] ABSTRACT

A conductimetric gas sensor consists of a ptfe body forming an electrolytic cell; two threaded silver electrodes screwed into the ptfe body and bridged by a layer of a hydrophilic gel in contact with an electrolyte in the cell; a reservoir for supplying deionized water to the cell, so that the volume of water between the electrodes is maintained; and a gas-permeable hydrophobic layer through which the hydrophilic gel can be exposed to the gas.

7 Claims, 1 Drawing Figure

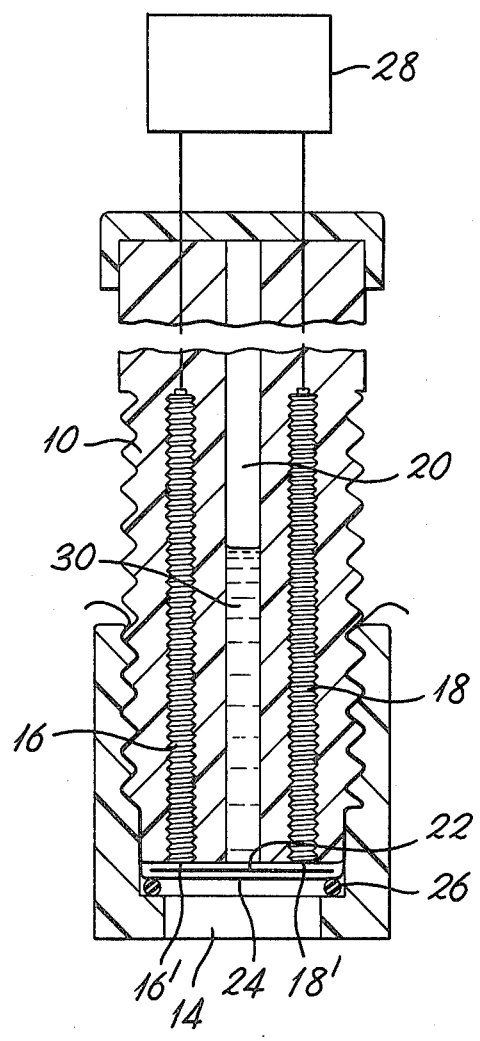

CONDUCTIMETRIC GAS SENSOR

FIELD OF THE INVENTION

This invention relates to the measurement of gas concentration by sensing the effect on an electrolyte of dissolution of the gas.

BACKGROUND OF THE INVENTION

It is known to measure gas concentration by sensing the change in conductivity of an electrolyte when the gas dissolves in it. A conductimetric sensor is described by Himpler et al in Analytical Chemistry 50, No. 12, 1978, pp. 1623 to 1627. Gases which can be sensed in this way include carbon dioxide but a disadvantage of such a sensor is that the output has poor stability which results in base-line drift.

Another device which can be used to sense carbon dioxide concentration is the Stow-Severinghaus sensor in which the change in pH of an electrolyte due to dissolved $CO_2$ is sensed by a glass electrode. Such a sensor, in a form suitable for transcutaneous measurement of $CO_2$, is described in "Birth Defects": Original Article Series, Volume XV No. 4 pages 109 to 116, 1979. The National Foundation, in an article by D. Parker et al. A disadvantage of such a sensor is that miniature glass electrodes must be made individually by hand, and have a high source impedance which renders them susceptible to electrical noise and interference.

SUMMARY OF THE INVENTION

It is an object of the present invention to provide a stable conductimetric sensor capable of sensing $CO_2$.

According to the invention, a conductimetric gas sensor comprises an electrolyte cell; two spaced electrodes within the cell and both closely adjacent a gas permeable hydrophobic layer through which a gas to be sensed can contact the electrolyte; and between the electrodes and the hydrophobic layer a layer of a hydrophilic gel of polymeric material.

In one embodiment the hydrophilic gel is polyacryloylmorpholine.

In use the sensor will further comprise sensing means to sense the electrical conductivity of the electrolyte in the reservoir between the electrodes.

Further according to the invention, the hydrophilic gel may include an enzyme material capable of reducing the response time of the sensor to both increases and decreases in gas concentration.

BRIEF DESCRIPTION OF THE DRAWING

The invention will now be described by way of example only with reference to the accompanying drawing which shows in vertical section a conductimetric carbon dioxide sensor according to the invention.

DETAILED DESCRIPTION OF THE INVENTION

In the Figure, a tubular body 10 of polytetrafluoroethylene (ptfe) has an external thread which carries an end cap 12 having a central aperture 14. Two threaded silver rods 16, 18, are screwed through the body 10 and protrude slightly through the lower endface of the body at diametrically opposite positions to form the electrodes 16', 18'.

Covering the ends of the electrodes 16', 18' and the central reservoir 20 of the body 10 is a layer 22 of polyacryloylmorpholine about 20 micrometers thick. This is held in position by a membrane 24 of polytetrafluoroethylene film such as "Teflon" (Registered Trade Mark) about 6 micrometers thick which is held taut by an "O" ring 26 in the endcap 12; the membrane edges pass between the screw threads on the body 10 and the endcap 12.

The upper ends of the silver rods 16, 18 are connected to a conductivity meter 28 and, in use, the reservoir 20 contains an electrolyte 30 which is de-ionized water.

In operation the sensor is exposed to a carbon dioxide-containing atmosphere, and the gas passes through the membrane 24 and dissolves in a thin layer of de-ionized water trapped between the membrane and the gel layer 22. When carbon dioxide dissolves in the water its conductivity changes and this is sensed by the conductivity meter 28; typically a measuring frequency of 1 kHz is used. The gel layer 22 prevents carbon dioxide from entering the reservoir 20 and thus increasing the response time of the sensor.

At equilibrium, the water contains carbon dioxide in simple solution, carbonic acid, and hydroxyl, hydrogen, carbonate and bicarbonate ions. In both prior art sensors and the present invention, it can be shown that for carbon dioxide concentrations greater than about 0.03% (the atmospheric value), the concentrations of the hydrogen and bicarbonate ions predominate and so the increase in conductivity brought about by the addition of carbon dioxide is proportional to the square root of the partial pressure of carbon dioxide to which the device is exposed.

In prior art conductimetric gas sensors, it is believed that one cause of instability was the change in the physical dimensions of the electrolyte volume between the electrodes. Such a change was due to evaporation of the electrolyte, pressure changes on the membrane, and changes in ambient temperature. These changes cause base-line drift. The slow ingress of impurity ions into the de-ionized water electrolyte from the body of the sensor and any adhesives used on constructing the sensor also causes base-line drift.

In a conductimetric sensor according to the present invention, the layer of gel overcomes any pressure changes and reduces evaporation of the electrolyte through the membrane. The volume of water between the electrodes is maintained, because a relatively large reservoir is provided. The provision of threaded silver electrodes overcomes the problem of impurity ions—the screw threads provide an adequate liquid seal and avoid the need for adhesive, thus allowing the use of ptfe for the body 10 in comparison with sensors having bodies made of less inactive polymers.

The electrical impedance of the device is about 1 to 5 megohms; this reduction in comparison with prior art sensors (10 gigohms for a glass electrode) gives a corresponding decrease in sensitivity to noise and interference, allowing use of a simple conductivity meter to sense the gas concentration.

In a modification the gel layer 22 also incorporates an enzyme which reduces the reaction time of the sensor. Such an enzyme is carbonic anhydrase, which is stabilised by polyacryloylmorpholine. In a further modification the "Teflon" layer 24 is replaced by a filter of ptfe "Millipore" (Registered Trade Mark) material to reduce the response time of the sensor when making measurements in an atmosphere. The device may be used to measure gas concentration in a static atmosphere or a gas flow, or dissolved gases in a static or flowing liquid, or may be used to make a transcutaneous measurement by the provision of a heater to heat the skin to about 38° to 44° C., as is conventional in medical measurements.

I claim:

1. A conductimetric gas sensor, for measurement of gas concentration in a static or flowing fluid, comprising:

an electrolytic cell for containing an electrolyte of deionised water;

a gas-permeable hydrophobic layer through which a gas to be sensed can contact said electrolyte contained in the cell;

two spaced electrodes within the cell and both closely adjacent the gas-permeable hydrophobic layer;

between the electrodes and the hydrophobic layer, a layer of a hydrophilic gel of polymeric material; and a reservoir supplying deionised water to the cell, so that the volume of water between the electrodes is maintained.

2. A sensor according to claim 1 in which the hydrophilic gel is polyacryloylmorpholine.

3. A sensor according to claim 1 in which the gas permeable hydrophobic layer is polytetrafluoroethylene film.

4. A sensor according to claim 1 in which the electrolyte cell is a polytetrafluoroethylene body and the two electrodes are threaded silver rods which are screwed into said body.

5. A sensor according to claim 1 further comprising conductivity sensing means arranged to sense the electrical conductivity of the electrolyte in the cell between the electrodes.

6. A sensor according to claim 1 in which the hydrophilic gel includes an enzyme material capable of reducing the response time of the sensor to both increases and decreases in gas concentration.

7. A sensor according to claim 6 in which the enzyme is carbonic anhydrase.

* * * * *